(12) United States Patent  
Campbell et al.

(10) Patent No.: US 8,088,810 B2
(45) Date of Patent: Jan. 3, 2012

(54) PHENOXYPYRAZOLE COMPOSITION AND PROCESS FOR THE SOLVENT EXTRACTION OF METALS

(75) Inventors: John Campbell, Rochdale (GB); Ronald Matthys Swart, Oldham (GB); Lucy Emeleus, London (GB); Susan Owens, Manchester (GB)

(73) Assignee: Cytec Technology Corp., Wilmington, DE (US)

( * ) Notice: Subject to any disclaimer, the term of this patent is extended or adjusted under 35 U.S.C. 154(b) by 0 days.

(21) Appl. No.: 12/067,719

(22) PCT Filed: Aug. 7, 2006

(86) PCT No.: PCT/US2006/030891
§ 371 (c)(1),
(2), (4) Date: Jun. 21, 2008

(87) PCT Pub. No.: WO2007/040817
PCT Pub. Date: Apr. 12, 2007

(65) Prior Publication Data
US 2008/0312452 A1 Dec. 18, 2008

(51) Int. Cl.
*A61K 31/415* (2006.01)
*C07D 233/00* (2006.01)
(52) U.S. Cl. ..................... 514/403; 548/356.1
(58) Field of Classification Search .................. 514/403; 548/356.1
See application file for complete search history.

(56) References Cited

U.S. PATENT DOCUMENTS

| | | | |
|---|---|---|---|
| 2,721,143 | A | 10/1955 | Kraft et al. |
| 4,048,187 | A | 9/1977 | Anderson et al. |
| 5,254,695 | A | 10/1993 | Quan et al. |

FOREIGN PATENT DOCUMENTS

| | | | |
|---|---|---|---|
| DE | 4126543 | * | 11/1993 |
| WO | 03/053986 A1 | | 7/2003 |
| WO | 03/054237 A1 | | 7/2003 |
| WO | 2004/094676 A1 | | 11/2004 |
| WO | 2004/108973 A1 | | 12/2004 |

OTHER PUBLICATIONS

Su et al., "Synthesis and Metal ion Complexation of Novel 8-Hydroxyquinoline-Containing Diaza-18-Crown-6 Ligands and Analogues," J. Org. Chem., vol. 64, 1999, pp. 8855-8861, XP-002419222.
Maib et al., "Benzo-gamma-pyrones, Part XIII. Reaction of Chromone and Its Methyl Derivatives with Thiosemicarbazide," Polish Journal of Chemistry, vol. 61, No. 1-3, 1987, pp. 111-122, XP009078597.
Pigini et al., "Analogues with a 1,2-benziosoxazole Nucleus of Biologically Active Indole Derivatibes. III. Tryptamine and gramine isosters," Eur. J. Med. Chem. Chimca Therapeutica, vol. 10. No. 1, 1975, pp. 29-32, XP009078606.
Sammour et al., "Some Reactions with 3-Methyl-1H-naphtho[2,1-b]pyran-l-one," Journal for Praktische Chemie, vol. 314, No. 2, 1972, pp. 271-280, XP009078626.
Schönberg et al., "Experiments with 2-Methyl-1,3-alpha-naphthopyrone and Related Substances," J. Am. Chem. Soc., vol. 78, 1956, pp. 4689-4692, XP-002419223.
Baker et al., "Reactions of 4-Thionchromones with Amino-compounds, and with Methyl Iodide," J. Chem. Soc., 19545, pp. 998-1002, XP009078636, Mar. 1998.
Wittig et al., Effect of Ammonia and Ammonia Derivatives on o-Acetyleacetophenols, Chem. Ber., vol. 60, 1927, pp. 1085-1094, XP009078599.
Written Opinion of PCT/US2006/030891, date of mailing Feb. 23, 2007.
International Search Report of PCT/US2006/030891, date of mailing Feb. 23, 2007.

* cited by examiner

*Primary Examiner* — Susannah Chung
(74) *Attorney, Agent, or Firm* — Charles E. Bell

(57) ABSTRACT

A metal extractant comprising Formula (1) wherein $R^5$, $R^6$, $R^7$ and $R^8$ each independently are hydrogen, an optionally substituted hydrocarbyl group, an electron withdrawing group, an electron donating group, or one or more of $R^5$ & $R^6$, $R^6$ & $R^7$, $R^7$ & $R^8$ are linked in such way as to form an optionally substituted ring; Y is N or $CR^9$ wherein $R^9$ is hydrogen, an optionally substituted hydrocarbyl, optionally substituted hydrocarbyloxy, optionally substituted hydrocarbyloxycarbonyl, optionally substituted hydrocarbylcarbonyloxy group, optionally substituted optionally substituted mono or dihydrocarbylaminocarbonyl group; Z is N or $CR^{10}$ wherein $R^{10}$ is hydrogen, an optionally substituted hydrocarbyl, optionally substituted hydrocarbyloxy, optionally substituted hydrocarbyloxycarbonyl, optionally substituted hydrocarbylcarbonyloxy group, optionally substituted optionally substituted mono or dihydrocarbylaminocarbonyl group; and tautomers or salts thereof, with the proviso that both Y and Z could be N provided that no more than one of Y or Z is N.

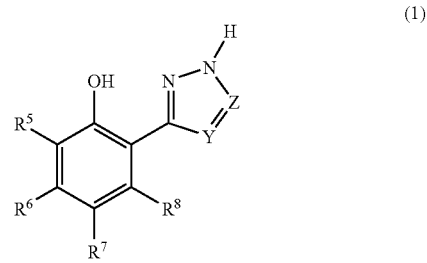

(1)

18 Claims, No Drawings

PHENOXYPYRAZOLE COMPOSITION AND PROCESS FOR THE SOLVENT EXTRACTION OF METALS

The present invention concerns solvent extractants, solvent extraction compositions, a solvent extraction process and especially a process for the extraction of metals, particularly copper and nickel, from aqueous solutions, especially solutions obtained by leaching ores.

It is known to extract metals, especially copper and nickel, from aqueous solutions containing the metal in the form of, for example, a salt, by contacting the aqueous solution with a solution of a solvent extractant in a water immiscible organic solvent and then separating the solvent phase loaded with metal, i.e. containing at least a part of the metal in the form of a complex. The metal can then be recovered by stripping with a solution of lower pH followed for example, by electrowinning. Most commonly, the aqueous metal-containing solutions for extraction are the result of the acid leaching of ores. However it is known that some metals, especially copper and nickel, can be leached from certain ores with ammoniacal solutions. This has the advantage that solutions containing especially high concentrations of copper and nickel are derived and that there is little contamination of the solution with iron.

Several types of organic solvent extractants have been proposed for use in the recovery of metals from aqueous solutions. Whilst many of the proposed reagents have been found to work well under laboratory conditions and demonstrate affinity for the recovery of copper and nickel or other metals from solutions, there are often problems encountered with the application of such reagents in commercial systems. One concern is the ability of the reagent to withstand high acidic or basic conditions. There is therefore a need for reagents, which can resist degradation under these conditions, and which show enhanced metallurgical properties.

Accordingly, there is provided a solvent extractant comprising one or more optionally substituted 2-hydroxyphenyldiazoles or optionally substituted 2-hydroxyphenyltriazoles.

Preferred are 2-hydroxyphenyldiazoles or 2-hydroxyphenyltriazoles of Formula (1)

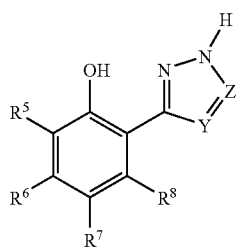

(1)

wherein
$R^5$, $R^6$, $R^7$ and $R^8$ each independently are hydrogen, an optionally substituted hydrocarbyl group, an electron withdrawing group, an electron donating group, or one or more of $R^5$ & $R^6$, $R^6$ & $R^7$, $R^7$ & $R^8$ are linked in such way as to form an optionally substituted ring;
Y is N or $CR^9$ wherein $R^9$ is hydrogen, an optionally substituted hydrocarbyl, optionally substituted hydrocarbyloxy, optionally substituted hydrocarbyloxycarbonyl, optionally substituted hydrocarbylcarbonyloxy group, optionally substituted optionally substituted mono or dihydrocarbylaminocarbonyl group;

Z is N or $CR^{10}$ wherein $R^{10}$ is hydrogen, an optionally substituted hydrocarbyl, optionally substituted hydrocarbyloxy, optionally substituted hydrocarbyloxycarbonyl, optionally substituted hydrocarbylcarbonyloxy group, optionally substituted optionally substituted mono or dihydrocarbylaminocarbonyl group;
and tautomers or salts thereof, with the provision that both Y and Z could be N provided that no more than one of Y or Z is N.

Whilst the invention is described herein with reference to a compound of Formula (1), it is understood that the invention relates to Formula (1) in any possible tautomeric forms, and also the complexes formed between compounds of Formula (1) and metals, particularly copper and nickel.

Preferred hydrocarbyl groups represented by $R^{5-10}$ independently include alkyl, alkenyl and aryl groups, and any combination thereof, such as aralkyl and alkaryl, for example benzyl groups.

Preferred alkyl groups represented by $R^{5-10}$ include linear and branched alkyl groups comprising up to 36 carbon atoms, particularly from 1 to 22 carbon atoms and preferably from 1 to 12 carbon atoms. When the alkyl groups are branched, the groups preferably comprise up to 5 branches in the carbon chain, and more preferably at least 1 branch in the carbon chain. In certain embodiments, the alkyl group is cyclic, preferably comprising from 3 to 10 carbon atoms in the largest ring and optionally featuring one or more bridging rings. Examples of alkyl groups represented by $R^{5-10}$ include methyl, ethyl, propyl, butyl, nonyl, hexylnonyl, butylnonyl, dodecyl and cyclohexyl groups and isomers thereof.

Preferred alkenyl groups represented by $R^{5-10}$ include $C_{2-20}$, and preferably $C_{2-6}$ alkenyl groups. One or more carbon-carbon double bonds may be present. The alkenyl group optionally carries one or more substituents, particularly phenyl substituents. Examples of most preferred alkenyl groups include vinyl, styryl and indenyl groups.

Preferred aryl groups represented by $R^{5-10}$ contain 1 ring or 2 or more fused rings. Preferably the aryl groups include aromatic and heteroaromatic groups. When the aryl group comprises fused rings, the fused rings preferably include cycloalkyl, aryl or heterocyclic rings. Examples of aryl groups include optionally substituted phenyl, naphthyl, thienyl and pyridyl groups.

Electron withdrawing groups represented by $R^{5-10}$ include halogen or nitro or optionally substituted hydrocarbyloxycarbonyl, optionally substituted hydrocarbylcarbonyl group, optionally substituted mono or dihydrocarbylaminocarbonyl group, including substitution by halogen, nitro SOR, $SO_2R$, groups.

Electron donating groups which may be represented by $R^{5-10}$ include hydrocarbyl, hydrocarbyloxy, optionally substituted hydrocarbylcarbonyloxy groups. When any of $R^{5-10}$ is a substituted hydrocarbyl or heterocyclic group, the substituent(s) should be such so as not to adversely interfere with the ability of the extractant to coordinate to metals. Optional substituents include, but are not limited to halogen, cyano, nitro, hydroxy, amino, thiol, acyl, hydrocarbyl, perhalogenated hydrocarbyl, heterocyclyl, hydrocarbyloxy, mono or dihydrocarbylamino, hydrocarbylthio, esters, carbonates, amides, sulphonyl and sulphonamido groups wherein the hydrocarbyl groups are as defined for $R^5$ above. One or more substituents may be present.

When any of $R^5$ & $R^6$, $R^6$ & $R^7$, $R^7$ & $R^8$, $R^8$ & $R^9$ and $R^9$ & $R^{10}$ are linked in such a way that when taken together with either the carbon atom and/or atom X of the compound of formula (1) that a ring is formed, preferably the ring be 5, 6 or 7 membered.

When any of $R^{5-10}$ is an aryl group, the aryl group is preferably a phenyl optionally substituted with one or more groups selected from $C_{1-12}$ alkyl or halo.

Phenyl groups optionally substituted with one or more groups selected from $C_{1-12}$ alkyl or halo represented by any of $R^{5-10}$ include those of formula:

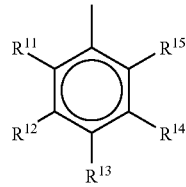

wherein $R^{11}$ to $R^{15}$ each independently represent H, halo, or a $C_{1-12}$ alkyl group.

When any of $R^{11}$ to $R^{15}$ are halo, preferably the halo is Cl or F.

When any of $R^{11}$ to $R^{15}$ are a $C_{1-12}$ alkyl group, the $C_{1-12}$ alkyl group can be linear or branched, and preferably is methyl, ethyl or isopropyl.

Preferably only $R^{13}$ represents a halo group or a $C_{1-12}$ alkyl group, with $R^{11}$, $R^{12}$, $R^{14}$ and $R^{15}$ representing H.

When any of $R^{5-10}$ is an optionally substituted phenyl group, it is most preferred that $R^{11}$ to $R^{15}$ are all hydrogen.

Highly preferred extractant compositions of the present invention include 2-hydroxyphenyldiazoles of Formula (2)

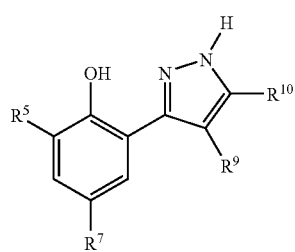

(2)

wherein
  $R^5$ is hydrogen, an optionally substituted hydrocarbyl group or an electron withdrawing group;
  $R^7$ is hydrogen, or an optionally substituted hydrocarbyl group;
  $R^9$ is hydrogen, an optionally substituted hydrocarbyl, optionally substituted hydrocarbyloxy, optionally substituted hydrocarbyloxycarbonyl, optionally substituted hydrocarbylcarbonyloxy group, optionally substituted optionally substituted mono or dihydrocarbylaminocarbonyl group;
  $R^{10}$ is hydrogen, an optionally substituted hydrocarbyl, optionally substituted hydrocarbyloxy, optionally substituted hydrocarbyloxycarbonyl, optionally substituted hydrocarbylcarbonyloxy group, optionally substituted optionally substituted mono or dihydrocarbylaminocarbonyl group;
and tautomers or salts thereof.

According to a further aspect of the present invention there is provided a solvent extractant composition comprising a water immiscible organic solvent, preferably with a low aromatic hydrocarbon content, and one or more solvent extractants of formula (1):

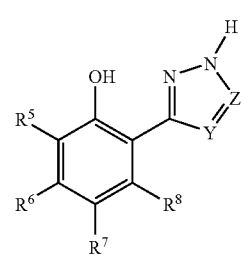

Formula (1)

as described above and tautomers or salts thereof.

Preferences for the solvent extractant of formula (1) are described as herein before in connection with the first aspect the present invention.

The composition may comprise one or more different optionally substituted 2-hydroxyphenyldiazoles or optionally substituted 2-hydroxyphenyltriazoles, especially where the component optionally substituted 2-hydroxyphenyldiazoles or optionally substituted 2-hydroxyphenyltriazoles are isomeric. Such isomeric mixtures may have better solubility in organic solvents than a single optionally substituted 2-hydroxyphenyldiazole or optionally substituted 2-hydroxyphenyltriazole or and are preferred.

The optionally substituted 2-hydroxyphenyldiazoles or optionally substituted 2-hydroxyphenyltriazoles are often present in an amount of up to 60% by weight of the composition, commonly no more than 50%, and usually no more than 40% w/w. Often, the optionally substituted 2-hydroxyphenyldiazoles or optionally substituted 2-hydroxyphenyltriazoles comprises at least 1% by weight, commonly at least 2.5% by weight and usually at least 5% by weight of composition, and preferably comprises from 7.5 to 20%, such as about 10%, by weight of the composition.

Organic solvents which may be present in the composition include any mobile organic solvent, or mixture of solvents, which is immiscible with water and is inert under the extraction conditions to the other materials present. Preferably the organic solvent has a low aromatic hydrocarbon content.

Preferred organic solvents are hydrocarbon solvents which include aliphatic, alicyclic and aromatic hydrocarbons and mixtures thereof as well as chlorinated hydrocarbons such as trichloroethylene, perchloroethylene, trichloroethane and chloroform.

Highly preferred organic solvents having a low aromatics content include solvents and solvent mixtures where the amount of aromatic hydrocarbons present in the organic solvent is less than 30%, usually around 23% or less, often less than 5%, and frequently less than 1%.

Examples of suitable hydrocarbon solvents include ESCAID 110, ESCAID 115, ESCAID 120, ESCAID 200, and ESCAID 300 commercially available from Exxon (ESCAID is a trade mark), SHELLSOL D70 and D80 300 commercially available from Shell (SHELLSOL is a trade mark), and CONOCO 170 commercially available from Conoco (CONOCO is a trade mark). Suitable solvents are hydrocarbon solvents include high flash point solvents and solvents with a high aromatic content such as SOLVESSO 150 commercially available from Exxon (SOLVESSO is a trade mark).

More preferred are solvents with a low aromatic content. Certain suitable solvents with a low aromatic content, have aromatic contents of <1% w/w, for example, hydrocarbon solvents such as ESCAID 110 commercially available from Exxon (ESCAID is a trade mark), and ORFOM SX 10 and ORFOM SX11 commercially available from Phillips Petroleum (ORFOM is a trade mark). Especially preferred, however on grounds of low toxicity and wide availability, are hydrocarbon solvents of relatively low aromatic content such as kerosene, for example ESCAID 100 which is a petroleum distillate with a total aromatic content of 23% commercially available from Exxon (ESCAID is a trade mark), or ORFOM SX7, commercially available from Phillips Petroleum (ORFOM is a trade mark).

In many embodiments, the composition comprises at least 30%, often at least 45% by weight, preferably from 50 to 95% w/w of water-immiscible hydrocarbon solvent.

Advantageously, it may be preferred to make and supply the composition in the form of a concentrate. The concentrate may then be diluted by the addition of organic solvents as described herein above to produce compositions in the ranges as described herein above. Where the concentrate contains a solvent, it is preferred that the same solvent is used to dilute the concentrate to the "in use" concentration range. In many embodiments, the concentrate composition comprises up to 30%, often up to 20% by weight, preferably up to 10% w/w of water-immiscible hydrocarbon solvent. Often the concentrate composition comprises greater than 5% w/w of water-immiscible hydrocarbon solvent. The viscosity of the "azoles" of the present invention means that concentrates do not display appreciably higher viscosity than extractant compositions at "in use" concentrations. In certain high strength concentrates it may be necessary to employ a higher than normal aromatic hydrocarbon content. In such cases where a high aromatic hydrocarbon containing solvent is used in the concentrate, solvent of very low aromatic hydrocarbon content may be used to dilute the concentrate to the "in use" concentration range.

If desired, compounds or mixtures of compounds selected from the group consisting of alcohols, esters, ethers, polyethers, carbonates, ketones, nitrites, amides, carbamates, sulphoxides, acids of sulphur and phosphorous compounds, for example sulphonic acids, and salts of amines and quaternary ammonium compounds may also be employed as additional modifiers or kinetics boosters in the composition of the invention. Particularly preferred are mixtures comprising a first compound selected from the group consisting of alcohols, esters, ethers, polyethers, carbonates, ketones, nitriles, amides, carbamates, sulphoxides, acids of sulphur and phosphorous compounds, for example sulphonic acids, and salts of amines and quaternary ammonium compounds and a second compound selected from the group consisting of alkanols having from 6 to 18 carbon atoms, an alkyl esters having from 7 to 30 carbon atoms, and tributylphosphate.

According to a third aspect of the present invention, there is provided a process for the extraction of a metal from solution in which an acidic solution containing a dissolved metal is contacted with a solvent extraction composition comprising a water immiscible organic solvent and a solvent extractant, whereby at least a fraction of the metal is extracted into the organic solution, characterised in that the solvent extraction composition comprises a water immiscible organic solvent, preferably with a low aromatic hydrocarbon content, and a solvent extractant of formula (1):

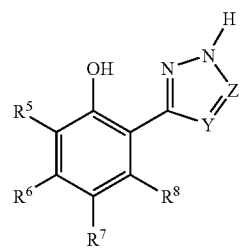

Formula (1)

as referred to above and tautomers or salts thereof.

Metals that may be extracted in the process according to the third aspect of the present invention include copper, cobalt, nickel, manganese and zinc, most preferably copper.

The extractant of formula (1) and the water immiscible organic solvent are as herein described before.

The aqueous acidic solution from which metals are extracted by the process of the third aspect of the present invention often has a pH in the range of from −1 to 7, preferably from 0 to 5, and most preferably from 0.25 to 3.5. Preferably, when the metal to be extracted is copper pH values of less than 3 are chosen so that the copper is extracted essentially free of iron, cobalt or nickel. The solution can be derived from the leaching of ores or may be obtained from other sources, for example metal containing waste streams such as from copper etching baths.

The concentration of metal, particularly copper, in the aqueous acidic solution will vary widely depending for example on the source of the solution. Where the solution is derived from the leaching of ores, the metal concentration is often up to 75 g/l and most often from 1 to 40 g/l. Where the solution is a waste stream, the metal concentrations can vary from 0.5 to 2 g/l for a waste water stream, to somewhat higher for those from other waste streams, for example Printed Circuit Board waste streams, and can be up to 150 g/l, usually from 75 to 130 g/l.

Preferred solvent extraction compositions are those where the organic solvent solutions may contain the optionally substituted 2-hydroxyphenyldiazoles or optionally substituted 2-hydroxyphenyltriazoles in an amount approaching 100% ligand, but preferably the optionally substituted 2-hydroxyphenyldiazoles or optionally substituted 2-hydroxyphenyltriazoles are employed at about 10 to 40% by weight. Highly preferred solvent extraction compositions are those comprising an organic solvent with a total aromatic content of around 23% or less and one or more optionally substituted 2-hydroxyphenyldiazoles or optionally substituted 2-hydroxyphenyltriazoles selected from 4-alkyl-2-(5-alkyl-1H-pyrazol-3-yl)-phenol and alkyl-3-(2-hydroxyphenyl)-1H-pyrazole-5-carboxylate in a total amount of between 5 to 40% by weight.

The process of the third aspect of the present invention can be carried out by contacting the solvent extractant composition with the aqueous acidic solution. Ambient or elevated temperatures, such as up to 75° C. can be employed if desired. Often a temperature in the range of from 5 to 60° C., and preferably from 15 to 40° C., is employed. The aqueous solution and the solvent extractant are usually agitated together to maximise the interfacial areas between the two solutions. The volume ratio of solvent extractant to aqueous solution are commonly in the range of from 20:1 to 1:20, and preferably in the range of from 5:1 to 1:5. In many embodiments, to reduce plant size and to maximise the use of solvent extractant, organic to aqueous volume ratios close to 1:1 are maintained by recycle of one of the streams.

After contact with the aqueous acidic solution, the metal can be recovered from the solvent extractant by contact with an aqueous acidic strip solution.

The aqueous strip solution employed in the process according to the third aspect of the present invention is usually acidic, commonly having a pH of 2 or less, and preferably a pH of 1 or less, for example, a pH in the range of from −1 to 0.5. The strip solution commonly comprises a mineral acid, particularly sulphuric acid, nitric acid or hydrochloric acid. In many embodiments, acid concentrations, particularly for sulphuric acid, in the range of from 50 to 200 g/l and preferably from 150 to 180 g/l are employed. When the extracted metal is copper, preferred strip solutions comprise stripped or spent electrolyte from a copper electro-winning cell, typically comprising up to 80 g/l copper, often greater than 20 g/l copper and preferably from 30 to 70 g/l copper, and up to 220 g/l sulphuric acid, often greater than 120 g/l sulphuric acid, and preferably from 150 to 180 g/l sulphuric acid. It has been found that these compounds strip at surprisingly low acid concentrations. This means that lower concentrations of strip acid can be used with concomitant savings in costs, or a more normal concentration of strip acid can be used with significant improvements in the recovery of copper. The very low residual copper on the extractant also means that loading in the subsequent extract cycle is more efficient. These compositions have the additional benefit of moving acid around the circuit. The volume ratio of organic solution to aqueous strip solution in the process of the third aspect of the present invention is commonly selected to be such so as to achieve transfer, per liter of strip solution, of up to 100 g/l of metal, especially copper into the strip solution from the organic solution. In many industrial copper electrowinning processes transfer is often from 10 g/l to 35 g/l, and preferably from 15 to 20 g/l of copper per liter of strip solution is transferred from the organic solution. Volume ratios of organic solution to aqueous solution of from 1:2 to 15:1 and preferably from 1:1 to 10:1, especially less than 6:1 are commonly employed.

Both the separation and stripping process can be carried out by a conventional batch extraction technique or column contactors or by a continuous mixer settler technique. The latter technique is generally preferred as it recycles the stripped organic phase in a continuous manner, thus allowing the one volume of organic reagent to be repeatedly used for metal recovery.

A preferred embodiment of the third aspect of the present invention comprises a process for the extraction of a metal from aqueous acidic solution in which:

in step 1, the solvent extraction composition comprising an extractant of formula (1) is first contacted with the aqueous acidic solution containing metal, in step 2, separating the solvent extraction composition containing metal-solvent extractant complex from the aqueous acidic solution;

in step 3, contacting the solvent extraction composition containing metal-solvent extractant complex with an aqueous acidic strip solution to effect the stripping of the metal from the water immiscible phase;

in step 4, separating the metal-depleted solvent extraction composition from the loaded aqueous strip solution.

According to a fourth aspect of the present invention, there is provided a process for the extraction of a metal from solution in which an aqueous ammoniacal solution containing a dissolved metal is contacted with a solvent extraction composition comprising a water immiscible organic solvent and a solvent extractant, whereby at least a fraction of the metal is extracted into the organic solution, characterised in that the solvent extraction composition comprises a water immiscible organic solvent, preferably with a low aromatic hydrocarbon content, and a solvent extractant of formula (1):

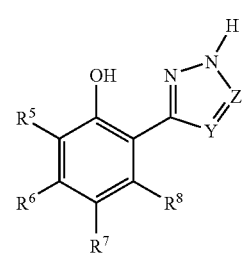

Formula (1)

as referred to above. and tautomers or salts thereof.

Metals that may be extracted in the process according to the fourth aspect of the present invention include copper, cobalt, nickel, manganese and zinc, most preferably copper and nickel.

The extractant of formula (1) and water immiscible organic solvent are as herein described before.

The aqueous ammoniacal solution from which metals are extracted by the process of this aspect of the present invention often has a pH in the range of from 7 to 12, preferably from 8 to 11, and most preferably from 9 to 10. The solution can be derived from the leaching of ores, particularly chalcocite ores, or may be obtained from other sources, for example precipitated metal oxide mattes or metal containing waste streams such as from copper etching baths.

Preferred solvent extraction compositions are those where the organic solvent solutions may contain the optionally substituted 2-hydroxyphenyldiazoles or optionally substituted 2-hydroxyphenyltriazoles in an amount approaching 100% ligand, but typically the optionally substituted 2-hydroxyphenyldiazoles or optionally substituted 2-hydroxyphenyltriazoles will be employed at about 10 to 40% by weight. Highly preferred solvent extraction compositions are those comprising an organic solvent with a total aromatic content of around 23% or less and one or more optionally substituted 2-hydroxyphenyldiazoles or optionally substituted 2-hydroxyphenyltriazoles from selected from 4-alkyl-2-(5-alkyl-1H-pyrazol-3-yl)-phenol and alkyl-3-(2-hydroxyphenyl)-1H-pyrazole-5-carboxylate in a total amount of between 5 to 40% by weight, in a total amount of between 5 to 40% by weight.

The concentration of metal, particularly copper or nickel, in the aqueous ammoniacal solution will vary widely depending for example on the source of the solution. Where the solution is derived from the leaching of ores, the metal concentration is often up to 75 g/l and most often from 1 to 40 g/l. Where the solution is a waste stream, the metal concentrations can vary from 0.5 to 2 g/l for a waste water stream, to somewhat higher for those from other waste streams, for example Printed Circuit Board waste streams, and can be up to 150 g/l, usually from 75 to 130 g/l. Where the solution is an ammoniacal nickel stream, the metal concentration is most often 1-20 g/l.

The process of the fourth aspect of the present invention can be carried out by contacting the solvent extractant composition with the metal containing aqueous ammoniacal solution. Ambient or elevated temperatures can be employed, often a temperature in the range of from 15 to 60° C., and preferably from 30 to 50° C., is employed. The aqueous solution and the solvent extractant are usually agitated together to maximise the interfacial areas between the two solutions. The volume ratio of solvent extractant to aqueous solution are commonly in the range of from 20:1 to 1:20, and preferably in the range of from 5:1 to 1:5. In many embodiments, to reduce plant size and to maximise the use of solvent extractant, organic to aqueous volume ratios close to 1:1 are maintained by recycle of one of the streams.

After contact with the aqueous ammoniacal solution, the metal can be recovered from the solvent extractant by contact with an aqueous strip solution having a pH lower than that from which the metal is extracted.

Alternatively, after contact with the aqueous ammoniacal solution, the metal can be recovered from the solvent extractant by contact with aqueous ammoniacal strip solution, particularly aqueous ammoniacal ammonium carbonate solution. The use of aqueous ammoniacal ammonium carbonate solution as a stripping solution is particularly suited to the recovery of metals in the form of metal carbonates, for example Nickel.

When an aqueous strip solution having a pH lower than that from which the metal is extracted is employed as a strip solution in the process according to the fourth aspect of the present invention, the aqueous strip solution is usually acidic and is as described for the strip solution in the process of the third aspect of the present invention. When the extracted metal is copper, preferred strip solutions comprise stripped or spent electrolyte from a copper electro-winning cell, typically comprising up to 80 g/l, often greater than 40 g/l copper and preferably from 50 to 70 g/l copper, and up to 220 g/l sulphuric acid, often greater than 120 g/l sulphuric acid, and preferably from 150 to 180 g/l sulphuric acid.

The volume ratio of organic solution to aqueous strip solution in the process of the fourth aspect of the present invention is commonly selected to be such so as to achieve transfer, per liter of strip solution, of up to 10 g/l of metal, especially of copper or nickel into the strip solution from the organic solution. In many industrial copper electrowinning processes transfer is often from 10 g/l to 35 g/l, and preferably from 15 to 20 g/l of copper per liter of strip solution is transferred from the organic solution. Volume ratios of organic solution to aqueous solution of from 1:2 to 15:1 and preferably from 1:1 to 10:1, especially less than 6:1 are commonly employed.

When ammoniacal ammonium carbonate solution is employed as a strip solution in the process of the fourth aspect of the present invention, the ammoniacal ammonium carbonate solution may contain excess ammonia and is preferably stronger than the ammoniacal ammonium carbonate solution used to leach the ore. The concentration of the solution used to recover the metal from the loaded organic phase is preferably in the ranges of $NH_3$:210 to 300 $gl^{-1}$, $CO_2$:150 to 250 $gl^{-1}$. Preferably, the solution strength is close to $NH_3$:270 $gl^{-1}$, $CO_2$:230 $gl^{-1}$.

The contact between the loaded organic phase and the ammoniacal ammonium carbonate solution may be carried out at any appropriate temperature and pressure. Preferably this step is conducted at atmospheric pressure and at a temperature in the range of 20° C. to 50° C.

It is preferred that the metal loaded organic phase is contacted with the ammoniacal ammonium carbonate solution for a period of between 30 seconds to 60 minutes. Most preferably the content time is for a period of about 3 minutes.

Both the separation and stripping process can be carried out by a conventional batch extraction technique or column contactors or by a continuous mixer settler technique. The latter technique is generally preferred as it recycles the stripped organic phase in a continuous manner, thus allowing the one volume of organic reagent to be repeatedly used for metal recovery.

When the process of the invention is applied to the operation of a continuous counter current mixer-settler apparatus, the organic/aqueous ratio in the stripping cells is preferably in the range of 6:1 to 10:1. This contrasts with the preferred organic/aqueous range in the extraction cells (where comparable organic agents may be used) of 1:1 to 1.2:1.

When the metal to be recovered is Nickel, it is preferred that the nickel loaded organic phase is stripped in a stripping cell at a temperature of about 40° C. An advantage of compounds of the present invention is that they are more stable under these conditions than commercial oxime extractants. The metal that separates into the aqueous phase can be recovered as a metal carbonate by any conventional manner. For example, basic nickel carbonate can readily be recovered by distillation. Nickel can also be recovered effectively from aqueous ammonium carbonate solution by hydrogen reduction under pressure. The recovery technique preferably allows for the $NH_3$ and $CO_2$ components of the strip liquor to be recycled to the metal loaded organic stripping stage.

A further advantage of the compounds of the present invention is the reduced transfer of ammonia across a circuit of solutions of the compounds of the present invention in diluent compared to solutions of the current oxime extractants.

A preferred embodiment of this aspect of the present invention comprises a process for the extraction of a metal from aqueous ammoniacal solution in which:

in step 1, the solvent extraction composition comprising an extractant of formula (3) is first contacted with the aqueous ammoniacal solution containing metal, in step 2, separating the solvent extraction composition containing metal-solvent extractant complex from the aqueous ammoniacal solution;

in step 3, contacting the solvent extraction composition containing metal-solvent extractant complex with an aqueous strip solution of lower pH than the ammoniacal solution to effect the stripping of the metal from the water immiscible phase;

in step 4, separating the metal-depleted solvent extraction composition from the loaded lower pH aqueous solution.

The metal can be recovered from the aqueous strip solution by conventional methods, for example by electrowinning.

A further preferred embodiment of this aspect of the present invention comprises a process for the extraction of a metal from aqueous ammoniacal solution in which:

in step 1, the solvent extraction composition comprising an extractant of formula (3) is first contacted with the aqueous ammoniacal solution containing metal, in step 2, separating the solvent extraction composition containing metal-solvent extractant complex from the aqueous ammoniacal solution;

in step 3, contacting the solvent extraction composition containing metal-solvent extractant complex with an aqueous ammoniacal strip solution, particularly aqueous an ammoniacal ammonium carbonate solution, to effect the stripping of the metal from the water immiscible phase;

in step 4, separating the metal-depleted solvent extraction composition from the loaded aqueous ammoniacal solution.

The invention is further illustrated, but not limited, by the following examples.

EXAMPLES

Example 1

Preparation of 1-(2-hydroxy-5-nonyl-phenyl)dodecane-1,3-dione

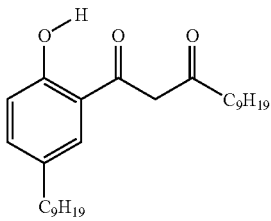

A solution of 2-Hydroxy-5-nonylacetophenone (0.3M) in toluene (50 ml) is added drop wise to a stirred slurry of sodium hydride (0.3M) in toluene (150 ml) at 30° C. over 30 minutes. Reaction mixture is stirred at 30° C. for 1 hour before versatic acid chloride (0.3M) is added drop wise over 1 hour. After the acid chloride addition is complete the reaction mixture is heated to 80° C. and held at this temperature for 1 hour. Cooled to ambient and potassium hydroxide flake (0.6M) added, heated to 80° C. and held at this temperature fore 2 hours. Cooled to ambient and reaction mass neutralised with aqueous acetic acid solution (25%). Toluene phase is washed with water (3×25 ml) then vacuum evaporated to leave brown oil.

$H^1$NMR (CDCl$_3$, 300 Hz)

δ0.5-1.8 (multiplets, alkyl 38H), δ6.4 (singlet, CH), δ6.9 (doublet, aryl H), δ7.1 (multiplet, aryl H), δ7.5 (multiplet, aryl H), δ9.8 & 10.8 (2×singlets, phenol OH & enol OH)

Example 2

Preparation of 4-Nonyl-2-(5-nonyl-1H-pyrazol-3-yl)-phenol

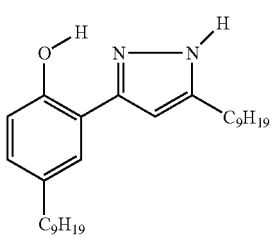

1-(2-hydroxy-5-nonyl-phenyl)dodecane-1,3-dione (0.1 M) dissolved in ethanol (50 ml), hydrazine hydrate (0.105M) added and the reaction solution heated to reflux. Held at reflux for 2 hours, cooled to ambient and organic phase washed with water (2×25 ml). Toluene removed by vacuum evaporation to produce a brown oil.

Mass Spec: Mol wt 412, found 411 (M-H)$^-$, 413 (M-H)$^+$.

$H^1$NMR (CDCl$_3$, 300 Hz)

δ0.5-1.8 (multiplets, alkyl 38H), δ6.2 (singlet, CH), δ6.9 (doublet, aryl H), δ7.5 (multiplet, 2×aryl H), δ11.9 & 15.6 (phenol OH & pyrazole NH)

Example 3

Preparation of n-octyl-4-(2-hydroxyphenyl)-2-4-dioxobutanoate

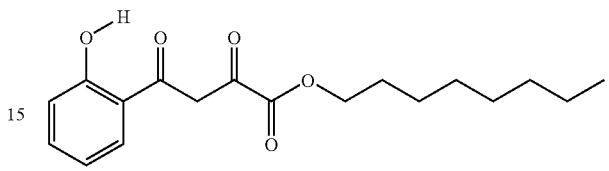

A mixture of 2-hydroxyacetophenone (0.15M) and ethyl pelargonate (0.45M) is added carefully to a slurry of sodium hydride (0.45M) in tetrahydrofuran over 90 minutes at 50-60° C., the mixture is kept under a atmosphere of nitrogen throughout the reaction. After addition complete the reaction mass is stirred for a further two hours at 50-60° C. Cooled to 25° C. and drowned into ice/water (600 g) before acidifying with acetic acid. Product extracted into hexane (200 ml). Hexane and any unreacted starting ester removed under vacuum to yield a yellow crystalline solid. Recrystallised from hexane.

Yield=18.9 g

Mass Spec Mol wt 275, found 275 (M-H)$^-$.

$H^1$NMR (CDCl$_3$, 300 Hz)

δ0.9-2.9 (alkyl chain protons, 17H), δ6.2 (singlet, CH), δ6.9-7.8 (multiplets, aryl 4H), δ12.1 & 15.0 (phenol OH & enol OH)

NMR suggests keto-enol rather than the 1,3 dione.

Example 4

Preparation of n-octyl-3-(2-hydroxyphenyl)-1H-pyrazole-5-carboxylate

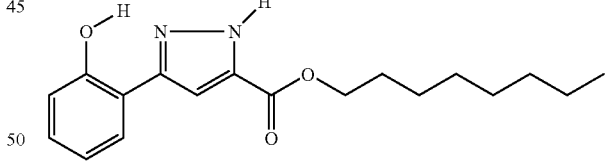

n-octyl-4-(2-hydroxyphenyl)-2-4-dioxobutanoate (0.05M) dissolved in ethanol (50 ml) and sodium acetate (5 g) added. Hydrazine hydrate (0.08M) added and the reaction solution heated to reflux. Held at reflux for 1 hours, cooled to AMBIENT and drowned into water (400 ml). Product extracted into hexane (200 ml) and the organic phase separated off and washed with water (2×50 ml). The solvent is removed by vacuum evaporation and the product recrystallised from hexane to yield a crystalline white solid.

Wt=11.7 g

Mass Spec Mol wt 272, found 271 (M-H)$^-$, 273 (M-H)$^+$.

$H^1$NMR (CDCl$_3$, 300 Hz)

δ0.9-2.8 (multiplets, alkyl 17H), δ6.45 (singlet, CH), δ6.9-7.7 (multiplets, aryl 4H), δ10.1 & 11.2 (phenol OH & pyrazole NH)

Copper Extraction (Comparison with a Commercially Available Reagent, 5-nonyl-2 hydroxyacetophenone-oxime)

From Acidic Copper Sulphate Solutions

Extraction Isotherms at pH 2.0

An aqueous solution containing a mixture of 3.0 g/l copper ($Cu^{2+}$) and 3.0 g/l iron ($Fe^{3+}$) sulphates at pH 2.0, is contacted with a ligand solution (0.2M) in Orfom SX7 at varying organic to aqueous ratios. The solutions are stirred for one hour at 25° C., to ensure equilibrium is reached. The organic and aqueous layers are separated and the copper content of each phase measured by atomic adsorption.

| Organic/Aqueous Ratio | 2-hydroxy-5-nonyl-acetophenone-oxime (commercial reagent) | | 2-(5-(1-hexylnonyl)-1H-pyrazol-3-yl)-phenol | |
|---|---|---|---|---|
| | Organic (Cu g/l) | Aqueous (Cu g/l) | Organic (Cu g/l) | Aqueous (Cu g/l) |
| 1.5:1.0 | 2.02 | 0.24 | 2.00 | 0.13 |
| 1.0:1.0 | 2.79 | 0.37 | 2.86 | 0.32 |
| 1.0:1.5 | 3.45 | 0.83 | 3.85 | 0.57 |
| 1.0:2.0 | 4.31 | 0.97 | 4.64 | 0.83 |
| 1.0:3.0 | 4.87 | 1.69 | 5.33 | 1.33 |
| 1.0:4.0 | 5.01 | 1.99 | 6.61 | 1.65 |
| 1.0:8.0 | 5.56 | 2.25 | 6.5 | 2.29 |

Strip Isotherms

An aqueous solution containing a typical acidic spent electrolyte (30 g/l copper ($Cu^{2+}$) and 150 g/l sulphuric acid) is contacted with a ligand solution (0.2M) in Orfom SX7, (which has previously been fully loaded with copper), at varying organic to aqueous ratios. The solutions are stirred for one hour at 25° C. to ensure equilibrium is reached. The organic and aqueous phases are separated and the copper content of the organic phase measured by atomic adsorption.

| Organic/Aqueous Ratio | 2-hydroxy-5-nonyl-acetophenone-oxime (commercial reagent) | | 4-Nonyl-2-(5-nonyl-1H-pyrazol-3-yl)-phenol | |
|---|---|---|---|---|
| | Organic (Cu g/l) | Aqueous (Cu g/l) | Organic (Cu g/l) | Aqueous (Cu g/l) |
| 1.00:2.00 | 0.413 | 33.04 | 0.019 | 33.89 |
| 1.33:1.00 | 0.508 | 37.49 | 0.027 | 39.13 |
| 2.50:1.50 | 0.647 | 43.52 | 0.058 | 46.44 |

The results illustrate the improved acid strip achieved with 4-nonyl-2-(5-nonyl-1H-pyrazol-3-yl)-phenol compared to a commercial reagent 2-hydroxy-5-nonyl-acetophenone-oxime.

From Ammoniacal Copper Chloride Solutions

Extraction Isotherms from Basic Solution

A typical Printed Circuit Board aqueous solution containing ammoniacal copper chloride (113 g/l $Cu^{2+}$/90 g/l $NH_3$) is contacted with a ligand solution (0.4M) in Orfom SX7 at varying organic to aqueous ratios. The solutions are stirred for one hour at 25° C., to ensure equilibrium is reached. The organic and aqueous layers are separated and the copper content of each phase measured by atomic adsorption.

| | 4-Nonyl-2-(5-nonyl-1H-pyrazol-3-yl)-phenol | |
|---|---|---|
| Organic/Aqueous Ratio | Organic (Cu g/l) | Aqueous (Cu g/l) |
| 10:1 | 8.99 | 24 |
| 8:1 | 9.8 | 35 |
| 4:1 | 11.14 | 69 |
| 2:1 | 12.18 | 90 |
| 1.5:1 | 12.36 | 95 |
| 1:1 | 12.25 | 101 |

Strip Isotherms

An aqueous solution containing a typical acidic spent electrolyte (30 g/l copper ($Cu^{2+}$) and 150 g/l sulphuric acid) is contacted with a ligand solution (0.4M) in Orfom SX7, (which has previously been fully loaded with copper, 12.48 g/l $Cu^{2+}$), at varying organic to aqueous ratios. The solutions are stirred for one hour at 25° C. to ensure equilibrium is reached. The organic and aqueous phases are separated and the copper content of the organic phase measured by atomic adsorption.

| | 4-Nonyl-2-(5-nonyl-1H-pyrazol-3-yl)-phenol | |
|---|---|---|
| Organic/Aqueous Ratio | Organic (Cu g/l) | Aqueous (Cu g/l) |
| 1.00:2.00 | 0.03 | 36.5 |
| 1.00:1.00 | 0.05 | 47.7 |
| 2.00:1.00 | 0.25 | 62.6 |

Nickel Extraction (Comparison with a Commercially Available Reagent, 5-nonyl-2 hydroxyacetophenone-oxime)

Extraction Isotherms from Ammoniacal Solution

An aqueous solution containing 10 g/l $Ni^{2+}$/40 g/l $NH_3$/20 gl $CO_2$ (prepared by dissolving ammonium carbamate (35.8 g/l) in an ammonia solution (77 g at 32% w/w) and diluting to 1 liter with water) is contacted with a ligand solution (0.49M) in Orfom SX7 at varying organic to aqueous ratios. The solutions are stirred for one hour at 25° C., to ensure equilibrium is reached. The organic and aqueous layers are separated and the nickel content of each phase measured by atomic adsorption.

| Organic/Aqueous Ratio | 2-hydroxy-5-nonyl-acetophenone-oxime (commercial reagent) | | 2-(5-nonyl-1H-pyrazol-3-yl)-phenol | |
|---|---|---|---|---|
| | Organic (Ni g/l) | Aqueous (Ni g/l) | Organic (Ni g/l) | Aqueous (Ni g/l) |
| 1.5:1.0 | 6.85 | 0.06 | 7.02 | 0.18 |
| 1.0:1.0 | 10.35 | 0.12 | 9.98 | 0.53 |
| 1.0:1.5 | 13.53 | 0.76 | 12.78 | 1.94 |
| 1.0:4.0 | 14.99 | 6.40 | 14.49 | 6.52 |
| 1.0:8.0 | 14.35 | 8.28 | 14.94 | 8.22 |

Strip Isotherms (A) Ammoniacal Stripping

An aqueous solution containing 280 g/l $NH_3$/220 g/l $CO_2$ (prepared by dissolving ammonium carbamate (197 g) in an ammonia solution (172 ml at 32% w/w) and diluting to 500 ml with water) is contacted with a ligand solution (0.49M in Orfom SX7) (which has previously been fully loaded with nickel) at varying organic to aqueous ratios. The solutions are stirred for one hour at 25° C. to ensure equilibrium is reached. The organic and aqueous phases are separated and the nickel content of the organic phase measured by atomic adsorption.

| Organic/Aqueous Ratio | 2-hydroxy-5-nonyl-acetophenone-oxime (commercial reagent) | | 2-(5-nonyl-1H-pyrazol-3-yl)-phenol | |
|---|---|---|---|---|
| | Organic (Ni g/l) | Aqueous (Ni g/l) | Organic (Ni g/l) | Aqueous (Ni g/l) |
| 4:1 | 5.73 | 43.30 | 2.46 | 58.12 |
| 6:1 | 7.16 | 54.31 | 4.93 | 68.5 |
| 10:1 | 9.51 | 68.98 | 8.21 | 80.73 |

The results illustrate the improved ammoniacal strip achieved with 4-nonyl-2-(5-nonyl-1H-pyrazol-3-yl)-phenol compared to a commercial reagent 2-hydroxy-5-nonyl-acetophenone-oxime.

(B) Nickel can also be Recovered Under Acid Stripping Conditions

This can be demonstrated by stripping nickel loaded organic with acidic spent electrolyte at varying organic to aqueous ratios. After stirring the solutions for one hour at 25° C. to ensure equilibrium is reached, the organic and aqueous phases are separated and the nickel content of the organic phase measured by atomic adsorption.

Ammonia Transfer

An aqueous solution containing 280 g/l $NH_3$/220 g/l $CO_2$ (prepared by dissolving ammonium carbamate (197 g) in an ammonia solution (172 ml at 32% w/w) and diluting to 500 ml with water) is contacted with a ligand solution (0.49M in Orfom SX7), (which had previously been fully loaded with nickel) at varying organic to aqueous ratios. The solutions are stirred for one hour at 25° C. to ensure equilibrium is reached. The organic phases are separated and the ammonia content of the organic phase measured by acid/base titration.

| Organic/Aqueous Ratio | 2-hydroxy-5-nonyl-acetophenone-oxime (commercial reagent) Organic Phase ($NH_3$ ppm) | 2-(5-(1-hexylnonyl)-1H-pyrazol-3-yl)-phenol Organic Phase ($NH_3$ ppm) |
|---|---|---|
| 1:1 | 2033 | 35 |
| 1:4 | 763 | 24 |

The results illustrate the reduced ammonia transfer into the organic phase achieved with 4-nonyl-2-(5-nonyl-1H-pyrazol-3-yl)-phenol compared to a commercial reagent 2-hydroxy-5-nonyl-acetophenone-oxime.

Reagent Stability Tests

Stability in Contact with a Typical Acidic Spent Electrolyte

A solution of each ligand (32 ml at 0.2M) in Orfom SX7 is stirred at 300 rpm in contact with an aqueous solution (32 ml) containing copper sulphate (30 g/l $Cu^{2+}$) and sulphuric acid (150 g/l) at 50° C. Samples are taken at various intervals and the maximum copper loading of each ligand solution is measured.

| Contact Time at 50° C. (hours) | 2-hydroxy-5-nonyl-acetophenone-oxime (commercial reagent) Maximum Load (% of start ML) | 2-(5-nonyl-1H-pyrazol-3-yl)-phenol Maximum Load (% of start ML) |
|---|---|---|
| 0 | 100 | 100 |
| 66 | 93.5 | 100 |
| 162 | 91.2 | 100 |
| 306 | 83.4 | 100 |

The results illustrate the significant improvement in the stability of 4-nonyl-2-(5-nonyl-1H-pyrazol-3-yl)-phenol when exposed to a typical acidic spent electrolyte compared to a commercial reagent 2-hydroxy-5-nonyl-acetophenone-oxime.

Stability in Contact with Typical Ammoniacal Strip Solution

A solution of each ligand (90 ml at 0.49M) in Orfom SX7, previously fully loaded with $Ni^{2+}$, is stirred at 600 rpm in contact with an aqueous solution (90 ml) containing 280 g/l $NH_3$/220 g/l $CO_2$ at 40° C. Samples are taken at various intervals and the maximum nickel loading of each ligand solution is measured.

| Contact Time at 40° C. (hours) | 2-hydroxy-5-nonyl-acetophenone-oxime (commercial reagent) Maximum Load (% of start ML) | 2-(5-nonyl-1H-pyrazol-3-yl)-phenol Maximum Load (% of start ML) |
|---|---|---|
| 0 | 100 | 100 |
| 19 | 99.8 | 100 |
| 67 | 100 | 100 |
| 140 | 99.7 | 100 |
| 308 | 98.9 | 100 |
| 476 | 95.6 | 100 |
| 692 | 90.6 | 100 |
| 1004 | 70.6 | 100 |
| 1822 | 32.5 | 100 |

The results illustrate the significant improvement in the stability of 4-nonyl-2-(5-nonyl-1H-pyrazol-3-yl)-phenol exposed to a typical ammonia/carbonate strip solution when compared to a commercial reagent 2-hydroxy-5-nonyl-acetophenone-oxime.

What is claimed is:

1. A metal extractant compound according to Formula

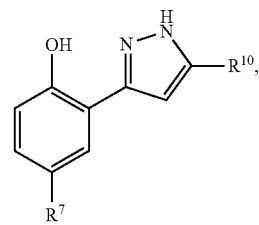

wherein $R^7$ is chosen from: a $C_9$-$C_{15}$ hydrocarbyl; and isomers thereof; and $R^{10}$ is chosen from: a $C_1$-$C_{15}$ hydrocarbyl; and isomers thereof.

2. A metal extractant compound according to claim 1, wherein each of $R^7$ and $R^{10}$ is independently chosen from: a $C_9$-$C_{15}$ hydrocarbyl group; and isomers thereof.

3. A metal extractant compound according to claim 2, wherein each of $R^7$ and $R^{10}$ is independently chosen from an alkyl group selected from the group consisting of: nonyl; hexylnonyl; butylnonyl; dodecyl; and isomers thereof.

4. A metal extractant compound according to claim 3, wherein $R^7$ and $R^{10}$ are both nonyl, or isomers thereof.

5. A metal extractant compound according to claim 1, wherein $R^7$ is chosen from: nonyl; and isomers thereof; and $R^{10}$ is chosen from: a $C_1$-$C_8$ alkyl group; and isomers thereof.

6. A solvent extractant composition comprising:
a) a water immiscible organic solvent; and
b) a metal extractant compound according to Formula

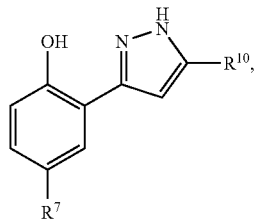

wherein $R^7$ is chosen from: a $C_9$-$C_{15}$ hydrocarbyl; and isomers thereof; and $R^{10}$ is chosen from: a $C_1$-$C_{15}$ hydrocarbyl; and isomers thereof.

7. A solvent extractant composition according to claim 6, wherein the metal extractant compound is present in an amount of from 1% to 60% by weight of the total composition.

8. A solvent extractant composition according to claim 7, wherein the metal extractant compound is present in an amount of from 5% to 40% by weight of the total composition.

9. A solvent extractant composition according to claim 8, wherein the metal extractant compound is present in an amount of from 7.5% to 20% by weight of the total composition.

10. A solvent extractant composition according to claim 6, wherein the aromatic hydrocarbon content of the organic solvent is less than 30% w/w, less than 23% w/w, less than 5% w/w, or less than 1% w/w.

11. A solvent extractant composition according to claim 6 further comprising:
c) a modifier or kinetic booster compound having a functional group chosen from: alcohols; esters; ethers; polyethers; carbonates; ketones; nitriles; amides; carbamates; sulphoxides; acids of sulphur and phosphorous compounds; tributylphosphate; and salts of amines and quaternary ammounium compounds.

12. A solvent extractant composition according to claim 11, wherein the functional group is an alcohol chosen from alkanols of 6 to 18 carbon atoms.

13. A solvent extractant composition according to claim 11, wherein the functional group is an ester chosen from alkyl esters of 7 to 30 carbon atoms.

14. A solvent extractant composition according to claim 6, wherein the metal extractant compound is chosen from: 4-nonyl-2-(5-nonyl-1H-pyrazol-3-yl)-phenol; 2-(5-(1-hexylnonyl)-1H-pyrazol-3-yl)-phenol; and mixtures thereof.

15. A metal extractant compound according to claim 5, wherein $R^{10}$ is methyl, or an isomer thereof.

16. A metal extractant compound according to claim 5, wherein $R^{10}$ is ethyl, or an isomer thereof.

17. A metal extractant compound according to claim 5, wherein $R^{10}$ is propyl, or an isomer thereof.

18. A metal extractant compound according to claim 5, wherein $R^{10}$ is butyl, or an isomer thereof.

* * * * *